United States Patent [19]

Fisher

[11] Patent Number: 4,486,410

[45] Date of Patent: Dec. 4, 1984

[54] HEAT DEFIBRINOGENATION OF AHF PREPARATION

[75] Inventor: Joseph D. Fisher, Chicago Heights, Ill.

[73] Assignee: Armour Pharmaceutical Company, Tarrytown, N.Y.

[21] Appl. No.: 578,724

[22] Filed: Feb. 9, 1984

[51] Int. Cl.³ .............................................. A61K 35/16
[52] U.S. Cl. .................................. 424/101; 260/112 R
[58] Field of Search ...................... 424/101; 260/112 R

[56] References Cited

U.S. PATENT DOCUMENTS

| | | | |
|---|---|---|---|
| 4,085,095 | 4/1978 | Bick et al. | 424/101 |
| 4,170,639 | 10/1979 | Liu et al. | 424/101 |
| 4,188,318 | 2/1980 | Shanbrom | 424/101 |

*Primary Examiner*—Sam Rosen

[57] ABSTRACT

Antihemophilic factor (AHF), a blood component necessary for clotting of normal whole blood, is extracted from cryoprecipitate containing AHF and fibrinogen as its principal components by: rapidly raising and thereafter lowering the temperature of the cryoprecipitate suspension to selectively denature the fibrinogen in the suspension; and separating the AHF-rich supernatant from the denatured fibrinogen.

14 Claims, No Drawings

HEAT DEFIBRINOGENATION OF AHF PREPARATION

BACKGROUND OF THE INVENTION

1. Field of the Invention

This invention relates to a method of making antihemophilic factor (AHF, Factor VIII) concentrate which is substantially fibrinogen free. AHF is a blood phasma protein useful for therapeutic administration to patients having hemophilia.

Hemostatis, the biochemistry of blood coagulation, is an extremely complex and as yet not completely understood phenomena whereby normal whole blood and body tissue prevent an excess loss of blood from a ruptured blood vessel. The total mechanism of blood coagulation is affected through the coordinated interaction of biochemical substances contained in three basic physiologic systems, namely, extravascular tissue such as subcutaneous tissue, muscle tissue, and skin; the blood vessel wall; and intravascular components, including blood plasma proteins, blood plasma factors, and platelets. By far the most important, and yet least understood, of the biochemical considerations affecting clotting, involve the intervascular blood components.

Since most of the blood clotting diseases in man occur in the intervascular blood system, usually due to a deficiency or inactivation of one or more blood plasma factors, great effort has been expanded in this direction by scientific research in an attempt to understand the role blood plasma factors play in the biochemical mechanism of blood clotting. Although in recent years much progress has been made in understanding the complexities of blood clotting, many more years of painstaking effort will be required before man finally gains sufficient knowledge to effectively ameliorate blood clotting disease. In the meantime, the state of the art with respect to the treatment of most blood clotting diseases will continue to be the administration of therapeutic pharmaceutical and biochemical substances in an attempt to relieve the adverse effects of these diseases.

A great deal of medical research into blood clotting diseases has been directed towards finding an acceptable treatment for hemophilia, a genetically induced disease characterized by the loss of clotability of otherwise normal whole blood. Although the precise cause of hemophilia is not known, one of the most popular theories suggests that it may be because of the absence of or a greatly inhibited presence of the active form of AHF in otherwise normal plasma from whole blood. At present, although hemophilia cannot be cured, it can often be treated therapeutically be the administration of AHF to an AHF-deficient individual.

2. Description of the Prior Art

AHF derived from blood obtained from a normal and healthy donor is administered either by the transfusion of whole blood or blood plasma, or by the infusion of AHF plasma protein concentrate which has been extracted from the plasma of normal human whole blood. However, these techniques have often proved therapeutically unsatisfactory as will hereinafter appear.

When whole blood or blood plasma transfusions are used to relieve a hemophiliac, one must exercise great care to select reasonably fresh blood or plasma because the biologic activity of AHF is extremely labile upon storage under normal conditions. Even laboratory techniques, such as lyophilization and cryogenic preservation, will not prevent substantial loss of biologic activity of AHF over time. Another major disadvantage of whole blood or blood plasma transfusions is that the can introduce unwanted proteinaceous and non-proteinaceous material in the recipient's blood stream, often causing allergic reactions to sensitive patients, viral infections such as hepatitis, or hypervolumetric reactions to those persons who require extensive amounts of AHF to initiate clotting.

The third therapeutic technique; namely, i.v. administration of AHF plasma concentrates is presently being used extensively. These concentrates are being developed primarily to circumvent the aforementioned troublesome and often times dangerous side effects caused by whole blood or blood plasma transfusions. Essentially, AHF plasma concentrate might be characterized as AHF-rich blood plasma extracts from which some blood plasma proteins, such as the gamma globulins, most other blood plasma factors, and many inorganic chemicals have been removed. However, even currently available AHF-rich blood plasma concentrates may contain impurities which can cause deleterious effects when administered to man so that a need for a purer, more therapeutically acceptable AHF plasma concentrate still exists.

Of particular importance in the development of a more therapeutically acceptable AHF product has been the research directed towards the removal of fibrinogen from AHF plasma concentrate. Fibrinogen, contained in an AHF product, is an especially intolerable impurity because of its tendency to interfere with the blood platelets function of releasing essential clotting factors into the patient's blood stream. Although the exact mechanism has not been conclusively determined, it now seems that the fibrinogen coats the cellular membrane of the platelet and inhibits the passage of the clotting factors from the platelet through its membrane into the blood plasma.

Another disadvantage arising from the presence of fibrinogen impurities in an AHF plasma concentrate is the tendency of fibrinogen to develop strong antigenic rejection responses in many patients who have been subjected to repeated and prolonged fibrinogen-rich AHF plasma concentrate infusions. It has also been medically shown that repeated massive doses of fibrinogen contained in an AHF plasma concentrate can cause the same antigenetic response of the patient to become sensitive to other proteins in the AHF plasma concentrate, such as AHF, which might not normally be rejected if administered separately. Once anti-AHF antigens are formed within a patient, further therapeutic administration of AHF becomes less beneficial.

Because of the similar physical and chemical properties of AHF and fibrinogen, standard proteinaceous separation techniques, such as electrophorisis, chromatography, and solubility differentials, have not been able to effect a sharp separation of the two proteins to produce a therapeutically acceptable fibrinogen-free AHF product.

Accordingly, the need exists for a process whereby a fibrinogen-free AHF plasma concentrate of high biologic activity might be derived from a biological sample containing a high concentration of fibrinogen.

Accordingly, it is the prime objective of this invention to provide a therapeutically acceptable AHF product which is substantially free of fibrinogen.

Another object of this invention is to provide a method of producing a substantially fibrinogen-free AHF concentrate from a cryoprecipitate suspension containing as its major components fibrinogen and AHF without substantial loss of AHF biologic activity.

Still another object of this invention is to provide an AHF concentrate useful for administration to man which will not cause damage to body tissue or organs.

A still further object of this invention is to provide a process whereby a therapeutically acceptable AHF product can be made more inexpensively and simply than was heretofore possible.

These and still further objects as shall hereinafter appear are fulfilled by the present invention in a remarkably unexpected fashion as will be readily discerned from the following detailed description of certain exemplary embodiments of this invention, especially when read in conjunction with the accompanying drawing showing a flow diagram of a process embodying the present invention.

As used herein, the term cryoprecipitate defines the solid phase fraction of human plasma obtained as a result of thawing frozen human plasma at 0° C.±1° C. and removing the liquid phase. This solid fraction contains as its primary components AHF, fibrinogen, and various cold insoluble globulin proteins.

The present invention is predicated upon the discovery of a process whereby AHF can be substantially extracted from the fibrinogen and cold insoluble components of the cryoprecipitate without significant loss of AHF biologic activity.

More particularly, this invention is a process whereby the fibrinogen component in a cryoprecipitate is selectively denatured and extracted from the AHF component of the cryoprecipitate by a rapid heating and cooling step. Upon removal of the denatured fibrinogen component of the cryoprecipitate by precipitation, the resulting supernatant contains a therapeutic quality, substantially fibrinogen-free AHF product of high AHF biologic activity.

Our invention is based on the fact that each individual protein molecular retains its biological activity or capacity to function only within specific upper and lower temperature limits. When the temperature of the protein surpasses that upper temperature limit, it begins to change its three dimensional steriochemical configuration. When the change becomes permanent and all biological activity is lost, the protein is said to be denatured.

SUMMARY OF THE INVENTION

The starting material is frozen cryoprecipitate.

The method for preparing AHF with low fibrinogen content comprises the steps of:
 a., thawing the frozen cryoprecipitate;
 b., suspending the thawed cryoprecipitate in a low molar buffer, and adjusting the pH of the suspension to between 6.4 and 7.5;
 c., rapidly heating with agitation the suspension to between 50° to 55° C. and maintaining the temperature of the suspension for 1.5±0.5 minutes resulting in a two-phase solid liquid suspension;
 d., rapidly cooling the two-phase suspension to 40° C., preferably within one minute;
 e., further cooling the two-phase suspension to a temperature of between 10° to 15° C.;
 f., centrifuging the two-phase suspension at between 10° to 15° C.; and
 g., decanting the supernatant.

The supernatant rich in AHF may then be frozen, further concentrated, or lyophilized.

DETAILED DESCRIPTION OF THE INVENTION

Most blood plasma proteins denature at a narrow temperature range. It was discovered that when a cyroprecipitate suspension, containing as its primary components the two globular proteins AHF and fibrinogen, is subjected to a specific temperature cycle for a specific period of time, fibrinogen will denature at a significantly more rapid rate than AHF. Thus, by selectively denaturing and removing the solid fibrinogen from the cryoprecipitate, an AHF-rich product possessing most of its initial biologic activity can be obtained.

The starting material for the invention is frozen cryoprecipitate which is then thawed, suspended in a low molar buffer solution and the pH of the solution adjusted to between 6.4 and 7.5.

The thawed cryoprecipitate is suspended in the low molar buffer to prevent excessive deactivation of the extremely labile AHF and fibrinogen. One such buffer solution consists of a low molar physiological buffer such as imidazole, sodium phosphate, hepes, ammonium bicarbonate, EACA, glycine, or tris, although various other similar acting physiological buffers have been found effective. Additional ingredients in the buffer solution might consist of a low molar physiological salt such as NaCl to prevent protein agglutination, a low molar physiological anticoagulant such as sodium citrate to adsorb excess sodium ions and thus inhibit fibrinogen clotting, and hydrogen-free water to act as a diluent.

Before being subjected to the denaturing step, it is often convenient, but not necessary, to remove many of the trace proteins contained in the cryoprecipitate by various purification steps. One such procedure is the adsorbtion of blood factors VII, IX and X and thromboplastin on an aluminum hydroxide gel. The actual character of the resuspension buffer is not critical provided that the buffering compound is acceptable by the Food and Drug Administration and that the ionic strength is tolerable.

The suspended cryoprecipitate at approximately room temperature is placed in a suitable container and emersed in a thermostatic controlled heating apparatus, such as a water bath, held above a minimum temperature of 50° C. At no time should the temperature of the suspended cryoprecipitate be allowed to exceed 55° C. since the AHF contained in the suspended cryoprecipitate quickly loses its biological activity at temperatures above 55° C. The physical properties of AHF and fibrinogen determine the temperature and time parameters of the heating cycle of the invention. While the temperature of the suspended cryoprecipitate remains under 50° C., AHF and fibrinogen do not significantly lose their biologic activity over short periods of time. As the temperature of the suspended cryoprecipitate increases above 50° C., both fibrinogen and AHF begin to lose their biologic activity at a progressively more rapid rate; the rate of deactivation of fibrinogen being much greater than AHF. At temperatures above 55° C., both AHF and fibrinogen are rapidly deactivated.

A more homogenous temperature gradient may be maintained within the cryoprecipitate by agitating the container and stirring the contents during heating. It was found that if the temperature range of the cryoprecipitate suspension is maintained between 50° C. and 55°

C. for between 1.5±0.5 minutes, a substantial amount of the biologic activity of AHF contained in the cryoprecipitate can be preserved with substantially all fibrinogen contained in the cryoprecipitate deactivated.

Upon completion of the heating phase of the cycle, the suspension becomes a two-phase suspension; a solid phase and a liquid phase. The solid phase contains the denatured fibrinogen, some denatured AHF and other trace denatured proteins. The liquid phase contains the biologically active AHF, a small amount of undenatured fibrinogen, and many cold insoluble globular proteins. This two-phase cryoprecipitate suspension is immediately emersed in a thermostatically controlled cooling apparatus, such as an ice bath, and rapdily cooled, preferably within one minute, to 40° C. Cooling of the suspension continues until its temperature is between 10° to 15° C. The length of time to reach the temperature range of 10° to 15° C. preferably should be less than 10 minutes. The cooling phase of the cycle appears to aggregate and precipitate the cold insoluble proteins from the liquid phase thereby further increasing the specific activity of AHF in the liquid phase. Aggregation and precipitation may be enhanced by gentle stirring of the suspension.

The two-phase cryoprecipitate suspension is then centrifuged at about 12,000 g (10,000 rpm) for about 20 minutes to effect sharp separation of the solid and liquid phases. The solid phase now consists primarily of denatured fibrinogen and cold insoluble globular proteins. The liquid supernatant consists primarily of AHF and trace amounts of fibrinogen. The AHF-rich supernatant can be lyophilized at this point to produce a therapeutic quality product.

Prior to lyophilization, the AHF-rich supernatant may be further processed by many standard laboratory techniques to produce a purer product. One such technique, ultrafiltration concentration, has proved especially valuable.

Ultrafiltration can be accomplished using art-recognized procedures. For example, ultrafiltration may be accomplished by filtering the supernatant through an XM300 or PM 30 membranes using an Amicon Model 52 stirred cell at room temperature under 5-10 pounds of nitrogen.

Following the ultrafiltration, the ultrafiltered product may be lyophilized at −70° C. for 12 hours on a New Brunswick lyophilizer.

For further illustration of the process of the present invention a flow diagram of the process is shown below.

FLOW DIAGRAM

Resuspend cryoprecipitate in .05 M glycine
.03 M NaCl

Adjust pH to 6.9
Treat with Resorptar
Add .01 M citrate
Check for physiological pH

-continued
FLOW DIAGRAM

Heat rapidly with continuous, vigorous agitation -
Sample is warmer than 50° C. for 1.5 ± .5 min
Maximum sample temperature 55.0° C.
Recover: 90% AHF units/ml Cool sample rapidly to 10° C. for 30 minutes to precipitate cold insoluble globulins which are not removed by heat.

Centrifuge   12,000 × g for 20 min.
             Recover: 90% volume

Concentration with ultrafiltration Recover: 96% Total AHF Units
Volume reduced ⅓

Clarification, sterile filtration, vialing

Lyophilization - reconstitution in ⅓-⅔ original volume.
Final product: 30-50 μ/ml AHF activity
0-10% clottable protein
Specific activity 1 μ/mg
Total AHF units recovered: 75%

The following examples will further illustrate the invention.

EXAMPLE 1

Thawed cryoprecipitate is buffered with a 0.01 molar gylcine buffer, clarified with Al(OH)$_3$, and lyophilized at −70° C. for 12 hours. Upon reconstitution with hydrogen-free water, a 10 ml sample was heated for 2.0 minutes in a water bath whose temperature was held at 57.3° C. The maximum sample temperature was 55° C. The sample was held above 50° C. for 2.0 minutes. The sample was immediately cooled in an ice bath held at 5° C.

The denatured fibrinogen and cold insoluble proteins were separated with centrifugation at 12,000 gravities for 20 minutes. After decanting, the supernatant was ultrafiltered through a XM300 membrane using a Model 52 stirred cell. The ultrafiltered product was lyophilized at −70° C. for 15 hours on a New Brunswick lyophilizer.

EXAMPLE 2

Thawed cryoprecipitate is buffered with a 0.01 molar glycine buffer, clarified with Al(OH)$_3$, and lyophilized at −70° C., for 12 hours. Upon reconstitution with hydrogen-free water, a 10 ml sample was heated for 2.0 minutes in a water bath whose temperature was 57° C. The sample was held above 50° C. for 0.58 minutes. The sample was then cooled in an ice bath held at 10° C. for 30 minutes.

The denatured fibrinogen and cold insoluble proteins were separated with centrifugation at 12,000 gravities for 20 minutes. After decanting, the supernatant was ultrafiltered through a MX300 membrane using a Model 52 stirred cell. The ultrafiltered product is lyophilized at 31⁵° C. for 15 hours on a New Brunswick lyophilizer.

EXAMPLE 3

10 ml cryoprecipitate sample is suspended in a 0.01 molar glycine buffer and emersed in a water bath held at a constant 56° C. The temperature of the cryoprecipitate was held between 50° C. and 55° C. for 1.5 minutes. The average temperature of the sample was 54.6° C. Throughout the heating step, the sample was agitated. The sample was cooled in a 10° C. ice bath for 20 minutes. The denatured fibrinogen and cold insoluble proteins were separated with centrifugation at 12,000 gravities for 20 minutes. After decanting, the supernatant was ultrafiltered through a XM300 membrane using a Model 52 stirred cell. The ultrafiltered product is lyophilized at a −70° C. for 15 hours on a New Brunswick lyophilizer.

Products prepared by these and other examples according to the present invention were tested by the following assay methods.

AHF specific activity determinations are based on an assay of the relative clotting time of thrombin contained in a normal plasma control versus the thrombin clotting time in an identical plasma sample in which the AHF-rich product was added. This test procedure is fully described by Proctor in the American Journal of Chemical Pathology 36 212-219 (1961).

Fibrinogen concentration in the AHF product is measured by the thrombin clotting time with a DADE DATA-FI fibrinogen determination kit. This experiment measures the relative fibrinogen clotting time of a normal fibrinogen containing plasma sample versus an identical plasma sample in which the product of the present invention was added. This test procedure is described by Clauss in the ACTA Haematologia 17 237 (1957).

Representative results of AHF potency recovery are shown in Table I.

TABLE 1

| Sample | Water Temp. °C. | Time Sample Temp. >50° C. | Maximum Sample Temp. °C. | % AHF Potency Recovery |
| --- | --- | --- | --- | --- |
| 1 | 58.0 | 8.75 | 56.0 | 42 |
| 2 | 57.3 | 3.05 | 56.0 | 95 |
| 3 | 57.0 | 0.58 | 53.0 | 100 |
| 4 | 57.5 | 1.60 | 54.8 | 78 |
| 5 | 56.5 | 1.30 | 54.0 | 80 |
| 6 | 56.8 | 1.42 | 54.2 | 83 |
| 7 | 56.5 | 1.30 | 53.4 | 84 |
| 8 | 56.0 | 1.38 | 53.4 | 100 |
| 9 | 57.0 | 1.43 | 54.3 | 84 |
| 10 | 55.5 | 0.55 | 51.0 | 100 |
| 11 | 55.8 | 1.70 | 52.0 | 100 |
| 12 | 56.5 | 2.10 | 55.0 | 100 |

Specific activities (units of AHF activity/mg of protein) of the samples were about 1.0 μ/mg, while concentration of fibrinogen in the final product was reduced to 0–0.3 mg/ml or 0–10% of the concentration of fibrinogen in the starting material.

It should be understood by those skilled in the art that various modifications may be made in the present invention without departing from the spirit and scope thereof as described in the specification and defined in the appended claims.

What is claimed is:

1. A method for producing a substantially fibrinogen-free AHF product from a cryoprecipitate containing as its primary components AHF and fibrinogen comprising:
   a., suspending thawed cryoprecipitate in a low molar buffer solution;
   b., rapidly raising the temperature of the suspension to 50° to 55° C.;
   c., maintaining the temperature of the suspension for 1.5±0.5 minutes to obtain a two-phase suspension;
   d., rapidly cooling the two-phase suspension to a temperature of about 10°–15° C.;
   e., centrifuging the two-phase suspension at about 10°–15° C.; and
   f., decanting the supernatant containing AHF.

2. The method of claim 1 wherein the pH of the thawed cryoprecipitate in the low molar buffer is adjusted to 6.4–7.5.

3. The method of claim 1 wherein said low molar buffer is a glycine solution.

4. The method of claim 1 wherein said low molar buffer is a tris solution.

5. The method of claim 1 wherein said low molar buffer further comprises sodium chloride.

6. The method of claim 1 wherein said low molar buffer further comprises sodium citrate.

7. The method of claim 1 wherein said suspension of cryoprecipitate in the low molar buffer is agitated during the heating steps of b and c.

8. The method of claim 1 wherein said two-phase suspension of step c is cooled to 40° C. within one minute.

9. The method of claim 1 wherein said cooling of the two-phase suspension to about 10°–15° C. is accomplished in less than 10 minutes.

10. The method of claim 1 wherein said centrifuging of the two-phase suspension is at about 12,000 gravities for about 20 minutes.

11. The method of claim 1 further comprising the step of lyophilizing said supernatant containing AHF.

12. The method of claim 1 further comprising the step of ultrafiltering the supernatant.

13. The method of claim 12 further comprising the step of lyophilizing the ultrafiltered supernatant.

14. A method for producing a substantially fibrinogen-free AHF product for a cryoprecipitate containing as its primary components AHF and fibrinogen comprising:
   a., thawing a frozen cryoprecipitate and suspending it in a low molar buffer solution selected from the group consisting of imidazole, sodium phosphate, hepes, ammonium bicarbonate, glycine, and tris;
   b., adjusting the pH of said cryoprecipitate-containing buffer solution to 6.4–7.5;

c., rapidly raising the temperature of said suspension to 50° to 55° C.;

d., maintaining the temperature of the suspension for 1.5±0.5 minutes to obtain a two-phase suspension;

e., rapidly cooling the two-phase suspension to a temperature of 10°-15° C.;

f., centrifuging the two-phase suspension at 10°-15° C. at 10,000 rpm to separate a precipitate containing fibrinogen;

g., decanting the supernatant containing AHF;

h., ultrafiltering said supernatant through an XM300 membrane;

i. and lyophilizing the ultrafiltered supernatant at −70° C. for 15 hours.

* * * * *